United States Patent [19]

Bergman et al.

[11] Patent Number: 4,746,760

[45] Date of Patent: * May 24, 1988

[54] PROCESS FOR FUNCTIONALIZING ALKANES

[75] Inventors: Robert G. Bergman, Kensington, Calif.; Andrew H. Janowicz, Wilmington, Del.; Roy A. Periana, Berkeley, Calif.

[73] Assignee: Chevron Research Company, San Francisco, Calif.

[*] Notice: The portion of the term of this patent subsequent to Apr. 16, 2002 has been disclaimed.

[21] Appl. No.: 703,640

[22] Filed: Feb. 21, 1985

Related U.S. Application Data

[63] Continuation-in-part of Ser. No. 619,886, Jun. 12, 1984, Pat. No. 4,511,745.

[51] Int. Cl.$^4$ .............. B01J 19/12; C07C 17/00; C07F 15/00
[52] U.S. Cl. .................. 570/241; 570/252; 204/157.75; 204/157.73; 204/157.94; 204/157.95
[58] Field of Search .......... 204/162 R, 157.73, 157.75, 204/157.94; 570/241, 252; 260/429 CY

[56] References Cited

U.S. PATENT DOCUMENTS 3,459,780 8/1969 Wilkinson .......................... 570/241
4,138,420 2/1979 Unruh et al. .................. 260/429 CY

OTHER PUBLICATIONS

Jones, W. D. et al. "Alkane Carbon–Hydrogen Bond Activation by Homogeneous Rhodium(I) Compounds", Organometallics 1983, 2, pp. 562–563.
Janowicz, A. H. et al. "Activation of C—H Bonds in Saturated Hydrocarbons . . . and Functionalization of the Metal–Bound Alkyl Groups", J. Am. Chem. Soc. 1983, 105, 3929–3939.
Janowicz, A. H. et al. "C—H Activation in Completely Saturated Hydrocarbons: Direct Observation of M+R—H→M(R)(H)", J. Am. Chem. Soc. 1982, 104, 352–354.
Bergman, R. G. "Activation of Alkanes with Organotransition Metal Complexes", Science, Mar. 2, 1984, vol. 223, pp. 902–908.
Janowicz, A. H. et al. "Oxidative Addition of Soluble Iridium and Rhodium Complexes to Carbon–Hydrogen Bonds in Methane and Higher Alkanes", Pure & Appl. Chem., vol. 56, No. 1, pp. 13–23, 1984.
Wax, M. J. et al. "Reversible C—H Insertion . . . and Thermally Activating Methane", J. Am. Chem. Soc. 1984, 106, 1121.
Janowicz, A. H. et al. "Oxidative Addition of Soluble Iridium and Rhodium Complexes to Carbon–Hydrogen Bonds in Alkanes (1)—First IUCCP Symposium, 1983.
Janowicz, A. H. Ph.D. Thesis "A Mechanistic Study . . . Hydrogenolysis of M—C Bonds/C—H Bond Activation of Saturated Hydrocarbons", May 1982.
Periana, R. A. et al. "Rapid Intramolecular Rearrangement . . . Cationic Rhodium π-Allyl Complex", J. Am. Chem. Soc. 1984, 106, pp. 7272–7273.
Periana, R. A. et al. "Oxidative Addition of Rhodium . . . and Alkyl Group Functionalization", Organometallics, 1984, 3, pp. 508–516.
Hoyano, J. K. et al. "Oxidative Addition of the Carbon–Hydrogen Bonds . . . Photochemically Generated Iridium(I) Complex", J. Am. Chem. Soc. 1982, 104, pp. 3723–3725.
Jones, W. D. et al. "Kinetics and Thermodynamics of Intra- and Intermolecular Carbon–Hydrogen Bond Activation", J. Am. Chem. Soc. 1985, 107, 620–631.
Periana, R. A. et al. "Oxidative Addition of Rhodium to Alkane C—H Bonds: Enhancement in Selectivity and Alkyl Group Functionalization", Organometallics, 1984, 3, pp. 508–510.

Primary Examiner—John F. Niebling
Assistant Examiner—Ben C. Hsing
Attorney, Agent, or Firm—S. R. LaPaglia; T. G. DeJonghe; Q. T. Dickinson

[57] ABSTRACT

Process for functionalizing saturated hydrocarbons comprising:
(a) reacting said saturated hydrocarbons of the formula:

$R_1H$ 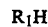

wherein H represents a hydrogen atom; and $R_1$ represents a saturated hydrocarbon radical, with a metal complex of the formula:

$CpRh[P(R_2)_3]H_2$ 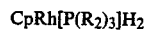

wherein
Cp represents a cyclopentadienyl or alkylcyclopentadienyl radical;
Rh represents a rhodium atom;
P represents a phosphorus atom;
$R_2$ represents a hydrocarbon radical;
H represents a hydrogen atom,
in the presence of ultraviolet radiation to form a hydridoalkyl complex of the formula:

$CpRh[P(R_2)_3](R_1)H$ 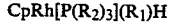

(b) reacting said hydridoalkyl complex with an organic halogenating agent such as a tetrahalomethane or a haloform of the formulas:

$CX'X''X'''X''''$ or $CHX'X''X'''$ 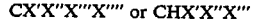

wherein X', X'', X''', X'''' represent halogens selected from bromine, iodine or chlorine atom, at a temperature in the range of about −60° to −17° C. to form the corresponding haloalkyl complex of step (a) having the formula:

$CpRhPMe_3RX$; and, 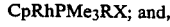

(c) reacting said haloalkyl complex formed in (b) with halogen ($X_2$) at a temperature in the range of about −60° to 25° C. (i.e., ambient) to form a functional haloalkyl compound.

24 Claims, No Drawings

4,746,760

PROCESS FOR FUNCTIONALIZING ALKANES

The invention disclosed herewith arose at the Lawrence Berkeley Laboratory in the course of, or under Contract No. De-AC03-76SF00098 between the U.S. Department of Energy and the University of California.

This application is a continuation-in-part of U.S. patent application Ser. No. 619,886, filed June 12, 1984, now U.S. Pat. No. 4,511,745 entitled "Process For Functionalizing Alkanes", in the names of Robert G. Bergman, Andrew H. Janowicz, and Roy A. Periana-Pillai, the disclosure of which is incorporated herein in its entirety by reference.

FIELD OF THE INVENTION

The present invention relates to functionalizing saturated hydrocarbons, and more particularly relates to functionalizing or enhancing the reactivity of alkanes by converting them to halo-substituted alkanes.

BACKGROUND OF THE INVENTION

Saturated hydrocarbons are obtained from petroleum, natural gas reservoirs, and other petroliferous deposits. They are, on a relative basis to other hydrocarbons, available in a relatively large supply. They have many uses in addition to being suitable as fuels. One of those uses, and one which has a high order of value in terms of uses, is as a raw material in chemical reactions when they can be made to react in an efficient, economical and predictable if not selective fashion. Particularly desirable is the ability to prepare terminally-substituted compounds, because terminally-substituted, or primary functional compounds, are in the greatest demand commercially. However, saturated hydrocarbons have strong C—H and C—C bonds which make the necessary reactions difficult for one or more reasons.

Various approaches to reaction of hydrocarbons have been studied over the years including thermal, chemical and photochemical. Examples of these are set forth in Janowicz and Bergman, J. Am. Chem. Soc. 105, 3929–3939 (1983). Most of these prior methods have consumed large amounts of energy in one form or another; and, importantly have lacked selectivity. Either, in addition to or separately, the prior methods have suffered other disadvantages.

Unsaturated compounds, in addition to being a valuable raw material for reactions which functionalized alkanes are not, do not always form terminally-substituted compounds but form 2-substituted derivatives according to Markovnikoff's rule.

Recently we found that certain organo-iridium complexes are capable of intermolecular oxidative addition to single C—H bonds in saturated hydrocarbons leading to hydridoalkyl iridium complexes which can be used to convert alkanes to alkyl halides. This is reported in Janowicz and Bergman, J.A.C.S. 104, 352 (1982). While this procedure enjoys a degree of benefits over the prior art it leaves room for improvement in several respects. One such important feature in the use of iridium complexes as precursors to alkyl halides is the need to pass through an organomercurial intermediate. The process using iridium also provides much less selectivity than theoretically possible and desirable.

OBJECTS OF THE INVENTION

It is a principal object of this invention to provide a method of functionalizing saturated hydrocarbons.

It is another object of this invention to provide a method of providing a high degree of selectivity in the functionalizing of alkanes.

It is an important object to provide a method of functionalizing alkanes which can be carried out at relatively mild conditions.

Still another and very important object of this invention is to provide a method which enables starting material to be regenerated and reused.

Yet, another object is to provide a process which does not require the additional step and use of organomercurial intermediates as in the case of iridium centered complexes.

An additional object is to provide a process for functionalizing alkanes which is efficient, relatively economical and has wide application in terms of alkanes which can be treated.

Additional objects, advantages and novel features of the invention will be set forth in part in the description which follows, and in part will become apparent to those skilled in the art upon examination of the following, or will be learned by practice of the invention. The objects and advantages of the invention may be realized and attained by means of the instrumentalities and combinations particularly pointed out in the appended claims.

SUMMARY OF THE INVENTION

A process for functionalizing saturated hydrocarbons comprising:

(a) reacting said saturated hydrocarbons of the formula:

$R_1H$ wherein H represents a hydrogen atom; and $R_1$ represents a saturated hydrocarbon radical, with a metal complex of the formula:

$CpRh[P(R_2)_3]H_2$ wherein Cp represents a cyclopentadienyl or alkylcyclopentadienyl radical having from 1 to 5 alkyl groups;
  Rh represents a rhodium atom;
  P represents a phosphorus atom;
  $R_2$ represents a hydrocarbon radical; and
  H represents a hydrogen atom,
in the presence of ultraviolet radiation to form a hydridoalkyl complex of the formula:

$CpRhP(R_2)_3(R_1)(H)$ (b) reacting said hydridoalkyl complex with an organic halogenating agent such as a tetrahalomethane or a haloform of the formulas:

$CX'X''X'''X''''$ or $CHX'X''X'''$;

wherein X', X'', X''', and X'''' represent halogens selected from bromine, iodine and chlorine, to form the corresponding haloalkyl complex of step (a) having the formula:

$CpRh[P(R_2)_3](R_1)(X)$;

and, (c) reacting said haloalkyl complex formed in (b) with halogen to form the alkyl halide of said saturated hydrocarbon wherein Cp, Rh, P, R₂, and X are the same as above.

In one specific aspect, the process provides a highly selective manner of preparing terminal, primary or 1-substituted halogenated alkyl compounds.

DETAILED DESCRIPTION OF THE INVENTION

In brief, the process can be described illustratively in equation form as follows:

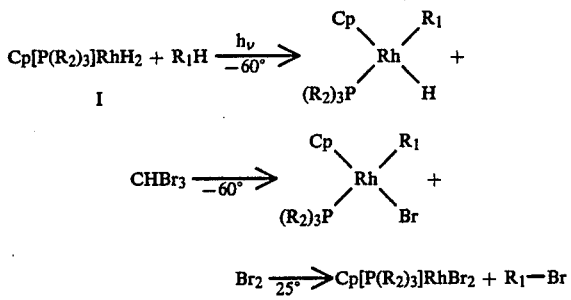

wherein Cp represents a cyclopentadienyl or alkylcyclopentadienyl radical (i.e., a cyclopentadienyl having 1 to 5 substituted alkyl groups) such as a pentaethylated or pentamethylated cyclopentadienyl radical;

$P(R_2)_3$ represents a trialkylated phosphorus radical or a trialkylphosphine radical;

Rh represents a Rhodium atom;

H represents a hydrogen atom;

$R_1$ represents an alkyl radical;

$R_2$ represents an alkyl radical; and

X represents a halogen atom as defined herein.

The $R_1$ as explained above, represents an alkyl radical and comes from the starting hydrocarbon used.

The reaction mechanism of this invention is generally applicable to all saturated hydrocarbons. However, preferred saturated hydrocarbons are those which have from 1 to about 20 hydrocarbons with the further provision that if they are not liquid when used alone, they are used in a mixture to be liquid at reaction conditions. More preferred are the saturated hydrocarbons of about 2 to 14 carbons which are liquid when used alone at reaction conditions (for example, at a temperature in the range of about −60° to −20° C.) Included in the hydrocarbons discussed above are the acyclic and cyclic alkanes. The acyclic alkanes can be either of straight or branch-chained configuration. Acyclic hydrocarbons of about 2 to 12 carbons which are liquid at reaction conditions are the most preferred hydrocarbons. The cyclic compounds can have as few as 3 carbon atoms and up to about 8 carbon atoms in the ring. Preferred cyclic compounds are those of about 3 to 6 carbon atoms in the ring. The cyclic compounds can be substituted by either straight or branch-chained alkyl radical(s).

Specific illustrative examples of suitable hydrocarbons which can be used (i.e., alone or in a mixture to produce a liquid at reaction conditions) are:

| | |
|---|---|
| methane | |
| ethane | methyl cyclooctane |
| propane | propylcyclooctane |
| cyclopropane | n-nonane |
| isobutane | neooctane |
| n-pentane | n-decane |
| neopentane | cyclodecane |
| cyclopentane | 4-methyl decane |
| n-hexane | methyl cyclodecane |
| cyclohexane | n-dodecane |
| 2-methyl hexane | 2-propyl nonane |
| 3-methyl hexane | n-tetradecane |
| methyl cyclohexane | 2-methyl, 4-butyl decane |
| dimethyl cyclohexane | 6-hexyl dodecane |
| 2-ethyl hexane | 2-ethyl-hexylcylodecane |
| 2,2'-dimethyl hexane | 1,4-dibutyl cyclooctane |
| 2-methyl, 4-ethyl hexane | n-eicosane |
| n-heptane | |
| cycloheptane | |
| n-octane | |
| cyclooctane | |

The dihydridometal complex starting material in the process can be prepared in the manner taught by Isobe, Bailey and Maitlis, J. Chem. Soc., Dalton Trans. 1981, 2003 or Kang, Moseley, and Maitlis, J.A.C.S. 91, 5970 (1969). In brief, that process involves reacting a pentaalkylated (e.g., pentamethylated) cyclopentadienyl rhodium dichloride dimer with trimethylphosphine and sodium bis-methoxy ethoxy aluminum hydride to form the dihydrido-rhodium complex, (I) shown in the equation above. Other triorgano-phosphines (e.g., triethylphosphine and triphenylphosphine) can be used but trimethylphosphine is preferred. Also, other hydrides can be used, for example, lithium triethylborohydride.

The complex formed as above is then reacted in a series of reactions at mild conditions according to this invention to produce an alkyl halide and an organometal dihalide complex above.

In the first step, the reaction of I and the alkane to be functionalized is carried out by subjecting the reactants to U.V. radiation (i.e., wavelength below about 210 nm) at a suitable temperature, for example, about −60° to −17° C. Preferred in most cases is a temperature in the range of about −35° to −20° C.

The above step can be carried out at superatmospheric or sub-atmospheric pressure, however, atmospheric pressure is generally preferred because the results at the other pressures usually do not warrant the use of such extraordinary measures. When the alkane is methane, superatmospheric pressure may be beneficial. Unless otherwise stated herein atmospheric pressure is generally preferred for all of the steps in this process.

One important consideration in connection with the above step is that dilution is desirable. To avoid many potential problems which include undesired side reactions, difficulties in separation of desired product, etc., a large excess of liquid hydrocarbon reactant is employed, where possible, instead of a separate solvent or diluent. Instead of stoichiometric, a dilution of about $1\times10^{-5}$ to $1\times10^{-2}$ molar concentration of the dihydride complex is beneficially employed. In the case of hydrocarbon reactants which are gaseous or solid (i.e., high molecular weight hydrocarbons) at reaction conditions, they require a solvent. Preferably, the solvent is inert or slow reacting so as to be practically inert at reaction conditions. However, in some cases, a lower molecular weight hydrocarbon desired to be functionalized can be conveniently used in lieu of a solvent as such.

In the next step, the complex formed in step (a) is reacted with an organic halogenating agent such as a polyhalogenated methane or a haloform of the formulas $CX'X''X'''X''''$ or $CHX'X''X'''$ where $X'$, $X''$, $X'''$, and $X''''$ represent halogen atoms; for example, $CBrCl_3$, $CHBrCl_2$, etc. Although the halogens can be bromine, iodine, or chlorine, bromine is preferred based on overall considerations. The reaction is carried out at a suitable temperature, for example, in the range of about −60° to −17° C. Temperatures closer to ambient (i.e., by ambient is meant about 18° to 20° C.) although still below ambient will generally be preferred to minimize the cost of cooling. With that and other factors in mind, a temperature in the range of about −35° to −20° C. will usually be preferred in this operation.

The preferred haloform, bromoform, can be conveniently added to the organo-metal complex by adding the neat liquid to a liquid bath or column of the complex to form halogenated product of the formula:

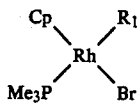

The halogenated organo-metal complex is next reacted with halogen (i.e., $Br_2$, a liquid at ambient; $I_2$, a solid at ambient; or $Cl_2$, a gas at ambient), preferably bromine, in the form of a liquid to generate the desired alkyl bromide product (or other halide corresponding to the reactants used). This reaction can be carried out by adding the bromine to the complex at a suitable temperature, for example, about −60° to 25° C. (i.e., ambient) with ambient being preferred for obvious reasons of economics.

Also formed with the desired alkyl halide is a dihalocounterpart of the starting organo-metal complex. This can be reused by regenerating through reaction of the by-product organo-metal complex with a known hydride source such as lithium aluminum hydride, lithium-triethylborohydride, sodium borohydride, sodium bis-methoxy ethoxy aluminum hydride (commercially available as Red-Al from Aldrich Chemical Company).

The following example is illustrative of the present invention, and is not to be regarded as limiting its scope.

EXAMPLE I

Experimental:

All manipulations were carried out under $N_2$ unless otherwise noted. Hexane was distilled from n-butyllithium. $CHBr_3$ was deoxgenated by purging with $N_2$.

Preparation of $\eta_5\text{-}C_5Me_5Rh[PMe_3](C_2H_5)Br$):

A 20 ml cylindrical shaped pyrex 37 bomb" equipped with a teflon vacuum stopcock was charged with 50 mg of ($\eta_5\text{-}C_5Me_5)Rh(PMe_3)H_2(I)$. The system was evacuated, cooled to −190° C. and ~10 ml of ethane was added by vacuum transfer into the flask. The bomb was carefully warmed to −60° C. and the solution agitated until all of the dihydride was dissolved. The solution was then photolysed for 2 hours at −60° C. with a 200 watt Hanovia immersion Hg lamp. The solution was cooled to −190° C. and 35 µl of $CHBr_3$ added via syringe. The mixture was rewarmed to −60° C. and agitated for 5 minutes. The ethane was then removed in vacuo and the resulting residue extracted with hexane (5×10 ml). The undissolved material was dissolved in a minimum of $CH_2Cl_2$ and cooled to −40° C. to yield 18 mg of ($\eta_5\text{-}C_5Me_5)Rh[PMe_3]Br_2$. The combined hexane extracts was filtered and concentrated under vacuum. The solution was cooled to −40° C. to yield 48 mg of ($\eta_5\text{-}C_5Me_5)Rh[PMe_3](C_2H_5)Br$).

Reaction of ($\eta_5\text{-}C_5Me_5)Rh[PMe_3](C_2H_5)(Br)$ with $Br_2$:

A 10 ml flask equipped with a rubber septum and magnetic stirrer was charged with 20 mg of ($\eta_5\text{-}C_5Me_5)Rh[PMe_3](C_2H_5)(Br)$, 8 ml of hexane and 5 µl of $CHBr_3$ (as internal standard). The stirred solution was cooled to −78° C. and a mixture of bromine/hexane (11 mg $Br_2$+1 ml hexane) was added over a period of 10 minutes. The stirred solution was allowed to warm up to room temperature and an aliquot removed by syringe was analyzed by gas chromatography. From gas chromatographic analysis, a calculated yield of bromoethane of approximately 80% based on ($\eta_5\text{-}C_5Me_5)Rh[PMe_3](C_2H_5)(Br)$ was obtained.

The foregoing description of a preferred embodiment of the invention has been presented for purposes of illustration and description. It is not intended to be exhaustive, or to limit the invention to the precise form disclosed, and obviously many modifications and verifications are possible in light of the above teachings. The embodiment was chosen and described in order to best explain the principles of the invention and its practical application to thereby enable others skilled in the art to best utilize the invention in various embodiments and with various modifications as are suited to the particular use contemplated. It is contemplated that embodiments of this invention employing different combinations of reactants will require the use of reaction conditions which may be outside the ranges disclosed herein, but the determination of such appropriate reaction conditions is well within the skill of the art, and in any event such embodiments are contemplated as equivalents of those described and claimed herein. It is intended that the scope of the invention be defined by the claims appended hereto.

What is claimed is:

1. A process for functionalizing saturated hydrocarbons comprising:
   (a) reacting said saturated hydrocarbons of the formula:

$R_1H$ 

wherein H represents a hydrogen atom; and $R_1$ represents a saturated hydrocarbon radical, with a metal complex of the formula:

$CpRh[P(R_2)_3]H_2$ 

wherein
   Cp represents an alkyl cyclopentadienyl radical;
   Rh represents a rhodium atom;
   P represents a phosphorus atom;
   $R_2$ represents an alkyl group;
   H represents a hydrogen atom,
   in the presence of ultraviolet radiation to form a hydridoalkyl complex of the formula:

$CpRh[P(R_2)_3](R_1)H$ 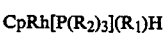

(b) reacting said hydridoalkyl complex with an organic halogenating agent to form the corresponding haloalkyl complex of step (a) having the formula $CpRh[P(R_2)_3](R_1)(X)$; 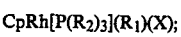

where X represents a halogen atom selected from bromine, iodine and chlorine and, C) reacting said haloalkyl complex formed in (b) with halogen to form the alkyl halide of said saturated hydrocarbon.

2. A process according to claim 1 wherein step (a) is carried out at a temperature in the range of about −60° to −17° C., step (b) is carried out at a temperature in the range of about −60° to −17° C. and step (c) is carried out at a temperature in the range of about −60° to 25° C.

3. A process according to claim 2 wherein the temperatures are in the ranges as follows:
step (a) −35° to −20° C.
step (b) −35° to −20° C.
step (c) 0° to 20° C.

4. A process according to claim 1 wherein X is bromine.

5. A process according to claim 1 wherein $R_2$ is a methyl group.

6. A process according to claim 1 wherein Cp represents a pentamethylated cyclopentadienyl radical.

7. A process according to claim 1 wherein the dilution of said metal complex in step (a) is in the range of about $1 \times 10^{-5}$ to $1 \times 10^{-2}$.

8. A process according to claim 1 wherein excess saturated hydrocarbon reactant is employed as solvent.

9. A process according to claim 1 wherein $R_1$ is at least one hydrocarbon radical of up to about 20 carbon atoms whereby $R_1H$ is a liquid at reaction conditions.

10. A process according to claim 1 wherein said saturated hydrocarbon reactant comprises methane present in a liquid admixture comprising at least one other saturated hydrocarbon.

11. A process according to claim 1 wherein said organic halogenating agent is a haloform of the formula $CHX'X''X'''$ where $X'$, $X''$, $X'''$ are halogens selected from the group of chlorine, bromine, or iodine.

12. A process according to claim 1 wherein said organic halogenating agent is a tetrahalogenated methane of the formula $CX'X41\ X'''X''''$ where $X'$, $X''$, $X'''$ and $X''''$ are selected from the group of chlorine, bromine, or iodine.

13. A process for functionalizing saturated hydrocarbons comprising:
(a) reacting said saturated hydrocarbons of the formula:

$R_1H$ wherein H represents a hydrogen atom; and $R_1$ represents a saturated hydrocarbon radical, with a metal complex of the formula:

$CpRh[P(R_2)_3]H_2$ wherein
Cp represents a cyclopentadienyl radical;
Rh represents a rhodium atom;
P represents a phosphorus atom;
$R_2$ represents an alkyl group;
H represents a hydrogen atom,
in the presence of ultraviolet radiation to form a hydridoalkyl complex of the formula:

$CpRh[P(R_2)_3](R_1)H$ (b) reacting said hydridoalkyl complex with an organic halogenating agent to form the corresponding haloalkyl complex of step (a) having the formula:

$CpRh[P(R_2)_3](R_1)(X)$;

where X represents a halogen atom selected from bromine, iodine and chlorine and,
(c) reacting said haloalkyl complex formed in (b) with halogen to form the alkyl halide of said saturated hydrocarbon.

14. A process according to claim 13 wherein step (a) is carried out at a temperature in the range of about −60° to −17° C., step (b) is carried out at a temperature in the range of about −60° to −17° C. and step (c) is carried out at a temperature in the range of about −60° to 25° C.

15. A process according to claim 14 wherein the temperatures are in the ranges as follows:
step (a) −35° to −20° C.
step (b) −35° to −20° C.
step (c) 0° to 20° C.

16. a process according to claim 13 wherein X is bromine.

17. A process according to claim 13 wherein $R_2$ is a methyl group.

18. A process according to claim 13 wherein $R_2$ is an ethyl group.

19. A process according to claim 13 wherein the dilution of said metal complex in step (a) is in the range of about $1 \times 10^{-5}$ to $1 \times 10^{-2}$.

20. A process according to claim 13 wherein excess saturated hydrocarbon reactant is employed as solvent.

21. A process according to claim 13 wherein $R_1$ is at least one hydrocarbon radical of up to about 20 carbon atoms whereby $R_1H$ is a liquid at reaction conditions.

22. A process according to claim 13 wherein said saturated hydrocarbon reactant comprises methane present in a liquid admixture comprising at least one other saturated hydrocarbon.

23. A process according to claim 13 wherein said organic halogenating agent is a haloform of the formula $CHX'X''X'''$ where $X'$, $X''$, $X'''$ are halogens selected from the group of chlorine, bromine, or iodine.

24. A process according to claim 13 wherein said organic halogenating agent is a tetrahalogenated methane of the formula $CX'X''X'''X''''$ where $X'$, $X''$, $X'''$ and $X''''$ are selected from the group of chlorine, bromine, or iodine.

* * * * *

UNITED STATES PATENT AND TRADEMARK OFFICE
CERTIFICATE OF CORRECTION

PATENT NO. : 4,746,760

DATED : May 24, 1988

INVENTOR(S) : Robert G. Bergman et al.

It is certified that error appears in the above–identified patent and that said Letters Patent is hereby corrected as shown below:

Claim 12, Column 7, Line 40, "CX'X41X'''X''''" should read --CX'X''X'''X''''--.

Claim 16, Column 8, Line 32, "a process" should read --A process--.

Signed and Sealed this

Twenty-sixth Day of December, 1989

Attest:

JEFFREY M. SAMUELS

*Attesting Officer*  *Acting Commissioner of Patents and Trademarks*